(12) United States Patent
Kereth et al.

(10) Patent No.: US 12,185,890 B2
(45) Date of Patent: Jan. 7, 2025

(54) MOBILE DISINFECTION DEVICE AND METHOD OF USE

(71) Applicant: PUREORR LTD., Savyon (IL)

(72) Inventors: Yefim Kereth, Rehovot (IL); Yoav Atzmon, Savyon (IL)

(73) Assignee: PUREORR LTD. (IL)

( * ) Notice: Subject to any disclaimer, the term of this patent is extended or adjusted under 35 U.S.C. 154(b) by 59 days.

(21) Appl. No.: 17/759,904

(22) PCT Filed: Feb. 1, 2021

(86) PCT No.: PCT/IL2021/050112
§ 371 (c)(1),
(2) Date: Aug. 1, 2022

(87) PCT Pub. No.: WO2021/152599
PCT Pub. Date: Aug. 5, 2021

(65) Prior Publication Data
US 2023/0066766 A1    Mar. 2, 2023

(30) Foreign Application Priority Data

Feb. 2, 2020 (IL) .......................................... 272425

(51) Int. Cl.
*A47L 11/40* (2006.01)

(52) U.S. Cl.
CPC ......... *A47L 11/405* (2013.01); *A47L 11/4011* (2013.01); *A47L 11/4044* (2013.01);
(Continued)

(58) Field of Classification Search
CPC .......................... A47L 11/405; A47L 11/4011; A47L 11/4044; A47L 11/4063; A47L 2201/04;
(Continued)

(56) References Cited

U.S. PATENT DOCUMENTS 3,761,987 A * 10/1973 Nayfa ................. A47L 11/4066
15/320
5,485,651 A * 1/1996 Payeur ...................... A47L 5/14
15/322

(Continued)

FOREIGN PATENT DOCUMENTS

WO    WO-2019120343 A1 *  6/2019  ............... A61L 2/10

OTHER PUBLICATIONS

Patent Cooperation Treaty, International Search Report and Written Opinion for International Application No. PCT/IL2021/050112, mailed May 17, 2021, 11 pages.

*Primary Examiner* — Erin F Bergner

(74) *Attorney, Agent, or Firm* — Stetina Brunda Garred & Brucker

(57) ABSTRACT

A mobile disinfection device (200) includes a disinfection chamber (203) coupled to a propulsion system (228) configured for moving along a surface (236) to be disinfected. The disinfection chamber defines a closed distal end (205), an open proximal end (206) and a surrounding wall (207) impervious to the radiation and having opposing front and rear portions and opposing side portions, respective proximal front, rear and side edges of which are propelled by the propulsion system close to the surface to be disinfected. A radiation source (260) is mounted inside the disinfection chamber for irradiating the surface through the open proximal end. The propulsion system includes a peripheral seal (304) surrounding a proximal edge of the wall and configured to obstruct radiation that might otherwise escape from inside the disinfection chamber.

19 Claims, 12 Drawing Sheets

(52) U.S. Cl.
CPC ....... *A47L 11/4063* (2013.01); *A47L 2201/04* (2013.01); *A47L 2201/06* (2013.01)

(58) Field of Classification Search
CPC ............. A47L 2201/06; A47L 11/4072; A47L 2201/00; A47L 11/4041; A47L 11/4058; A47L 11/30; A61L 2/24; A61L 2202/11; A61L 2202/121; A61L 2202/14; A61L 2202/16; A61L 2202/17; A61L 2202/25; A61L 2/10
See application file for complete search history.

(56) References Cited

U.S. PATENT DOCUMENTS

| | | |
|---|---|---|
| 7,923,707 B2 | 4/2011 | Garcia et al. |
| 2005/0022844 A1 | 2/2005 | Field et al. |
| 2009/0000056 A1* | 1/2009 | Garcia ................. A47L 9/00 15/339 |
| 2012/0223216 A1* | 9/2012 | Flaherty ............... G05D 1/0242 901/1 |
| 2014/0013536 A1* | 1/2014 | Hyun ..................... A47L 9/106 15/347 |
| 2017/0129396 A1* | 5/2017 | Salter .................... A61L 2/10 |
| 2020/0384140 A1* | 12/2020 | Hoehne ................ D06F 58/44 |

\* cited by examiner

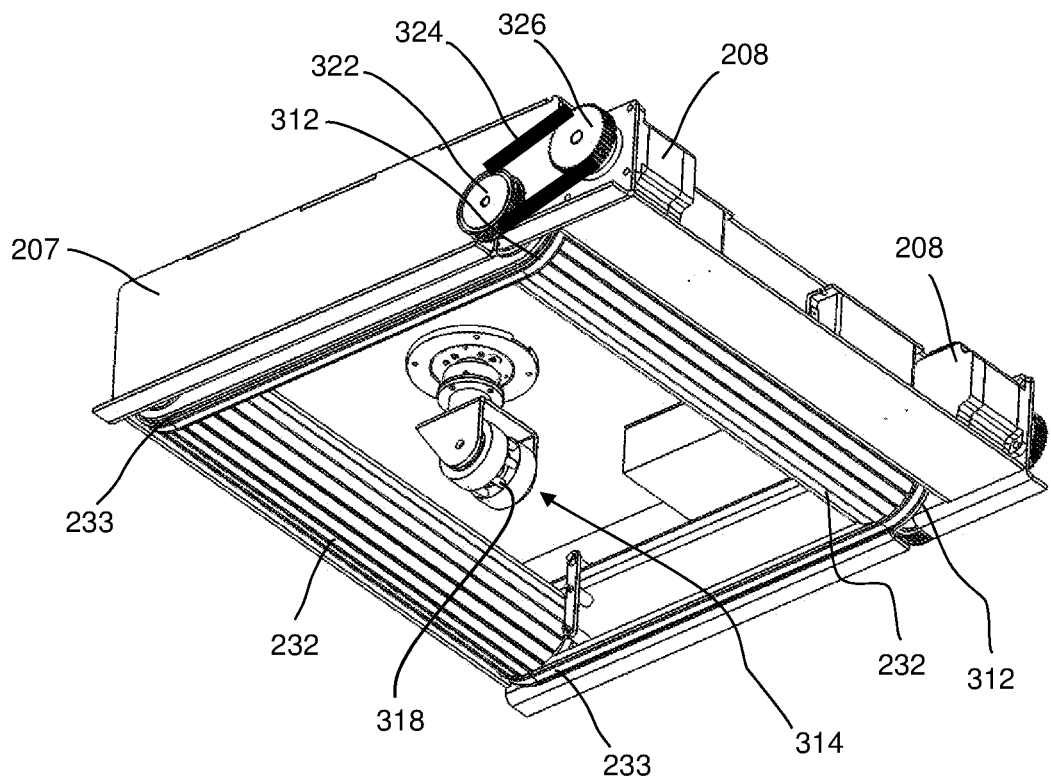
FIG. 13B
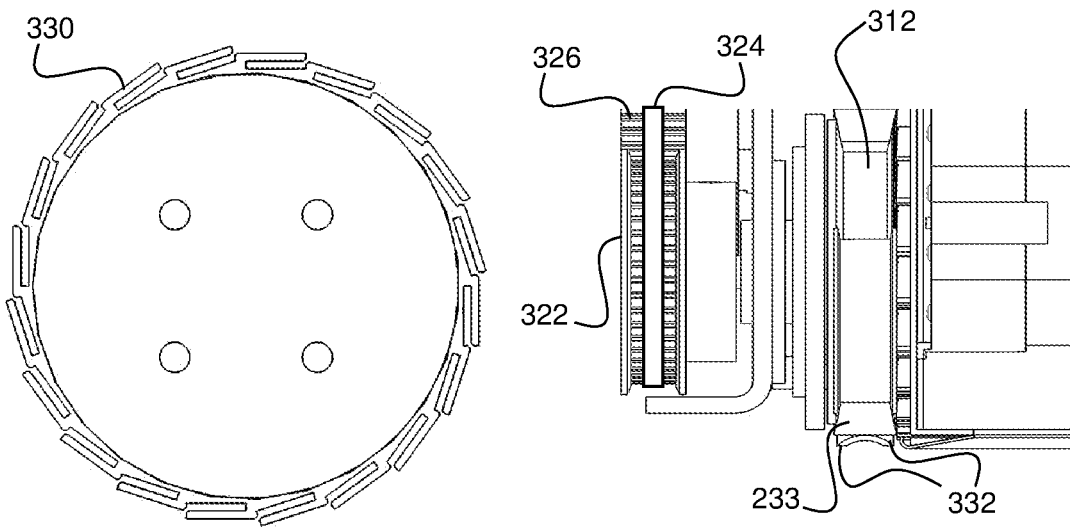
FIG. 13C    FIG. 13D

MOBILE DISINFECTION DEVICE AND METHOD OF USE

CROSS-REFERENCE TO RELATED APPLICATIONS

This application claims priority to PCT International Application No. PCT/IL2021/050112 filed on Feb. 1, 2021, which application claims priority to Israel Patent Application No. 272425 filed on Feb. 2, 2020, the entire disclosures of which are expressly incorporated herein by reference.

FIELD OF THE INVENTION

The present invention generally pertains to a mobile device and a method for disinfection of contaminated surfaces using radiation in a presence of humans.

BACKGROUND OF THE INVENTION

In general, microorganism colonies may be treated by UV radiation of sufficient power. However this treatment encounters two main challenges: the first is a safety in the presence of humans, the second is an efficacy in the presence of moisture and dust particles which constitutes an UV barrier (both the moisture and the dust), and a supportive environment for microorganism's growth and onward transmission (mainly for moisture).

The current situation is as follow: a) the typical safety approach is to avoid using powerful UV radiation in the presence of humans; b) the typical approach for cleaning is to use water, as it may effectively remove dirt and dust particles—however it may also be absorbed by the treated surfaces, e.g. floor; c) the water-free vacuum cleaning machines may remove the dirt and dust without applying water; however, it contributes to airborne dust and microorganism's transmission and may increase the disease distribution even more.

It is therefore a long felt need to provide a means for a powerful UV radiation in a presence of humans, while ensuring removal of moisture and dust to allow an effectual disinfection of the contaminated surfaces.

Mobile devices for disinfecting surfaces using UV radiation are known as are means for preventing radiation reaching personnel in close vicinity. Many of these devices are in the form of trolleys that are conveyed manually or automatically along a surface to be cleaned and have shields for preventing radiation leakage.

US2019134242 discloses with reference to FIG. 9 thereof a robot including a housing and a propulsion system in the form of a continuous track that enables the robot to traverse over different terrain throughout a room. Alternatively, the propulsion system can include wheels and an air/fluid bladder (e.g. hovercraft). The robot may include a suction (vacuum) port, fabric attachment pad, and a spray nozzle coupled to the bottom surface of housing that operate in conjunction with a light source to clean and sanitize floors. There is neither suggestion nor provision to prevent radiation leakage between the bottom surface of housing and the floor surface. This militates against use of the robot in an area open to human traffic since leakage of UV radiation would be hazardous to people close by.

SUMMARY OF THE INVENTION

It is a principal object of the present invention to provide a mobile device for safe radiation disinfection in a presence of humans. This object is achieved in accordance with a broad aspect of the invention by a mobile disinfection device, comprising:

a disinfection chamber coupled to a propulsion system configured for moving along a surface to be disinfected, said disinfection chamber defining a closed upper end, an open lower end and a surrounding wall having opposing front and rear portions and opposing side portions, respective lower front, rear and side edges of which are propelled by the propulsion system above the surface to be disinfected, and a radiation source mounted inside the disinfection chamber for irradiating said surface through the open lower end;

the wall of the disinfection chamber defining a peripheral shielding impervious to the radiation; and the propulsion system comprising a peripheral seal surrounding a proximal edge of said wall and being configured to obstruct radiation that might otherwise escape from inside the disinfection chamber.

In accordance with some embodiments, the device includes means for removal of moisture and dust to allow for improved disinfection of the contaminated surfaces.

In some embodiments, the lower edges of the surrounding wall of the disinfection chamber are provided with sealing lips that may be controlled to close an air gap that may be formed between the lower edges and the surface being disinfected.

In some embodiments, there is provided at least one sensor configured to determine abnormal behavior (e.g. device tilting or shaking), indicating a possible safety hazard, and at least indirectly stopping the UV irradiation, either electrically or by a shutter mechanism that blocks the UV source.

The device and method according to the invention are fully applicable for manually operated machines, as well as to autonomous systems (robots) acting in a presence of humans.

The term 'autonomous' or 'automatic' as used herein refers to a process or action executable without human intervention. For non-limiting example, in an autonomic cleaning and disinfection, the device controls all aspects of the process.

It is to be understood that any reference to cleaning and disinfection, as used herein, can refer to manually-controlled, to semi-automatic controlled or to fully automatic controlled.

BRIEF DESCRIPTION OF THE DRAWINGS

In order to better understand the invention and its implementation in practice, a plurality of embodiments will now be described, by way of non-limiting example only, with reference to the accompanying drawings, wherein

FIGS. 13A to 13D are views of the system with a floating track-barrier mechanism;

DETAILED DESCRIPTION

Figure 1:
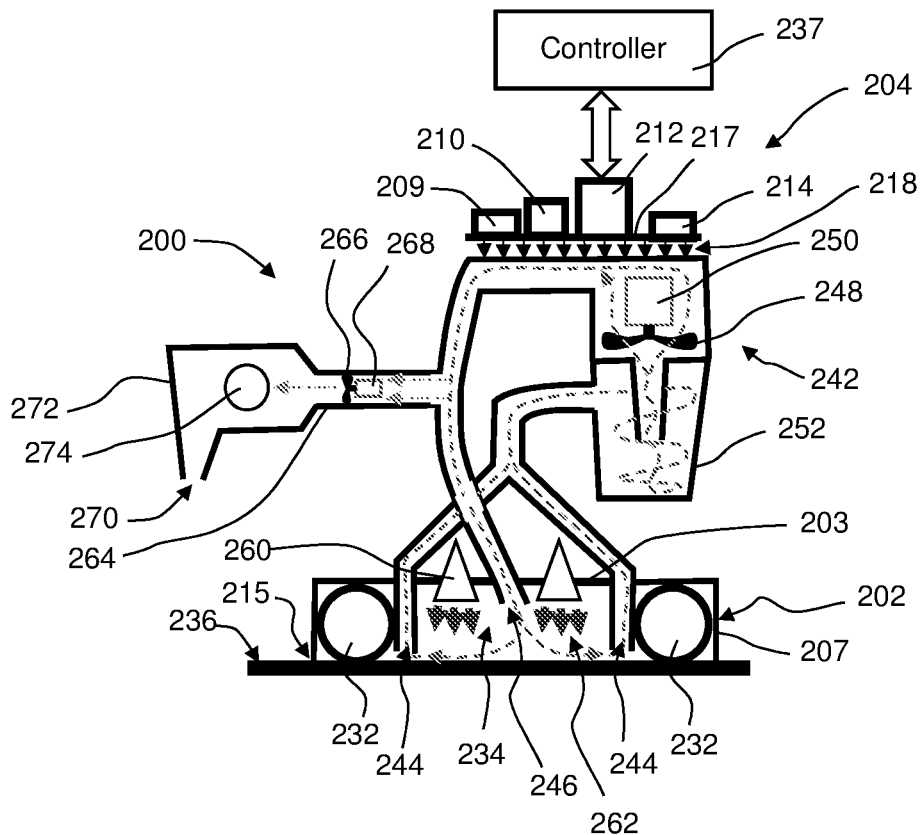
FIG. 1 illustrates a schematic embodiment of a device.
Figure 2:
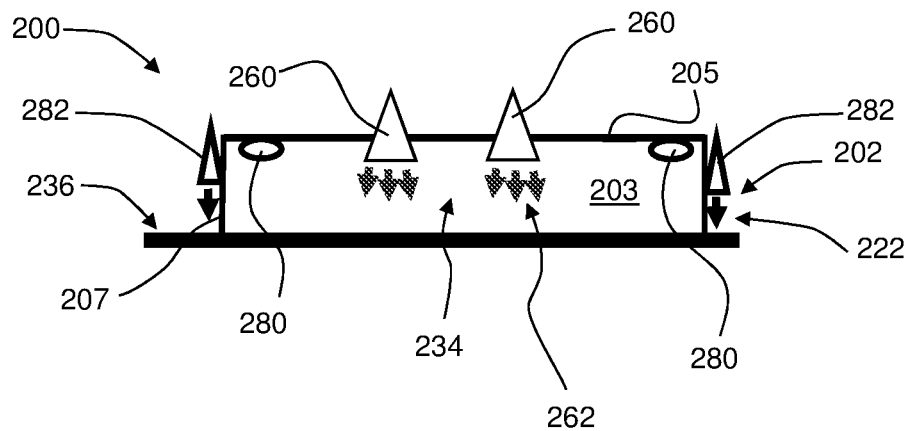
FIG. 2 illustrates a schematic embodiment of a safety mechanism.
Figure 3A:
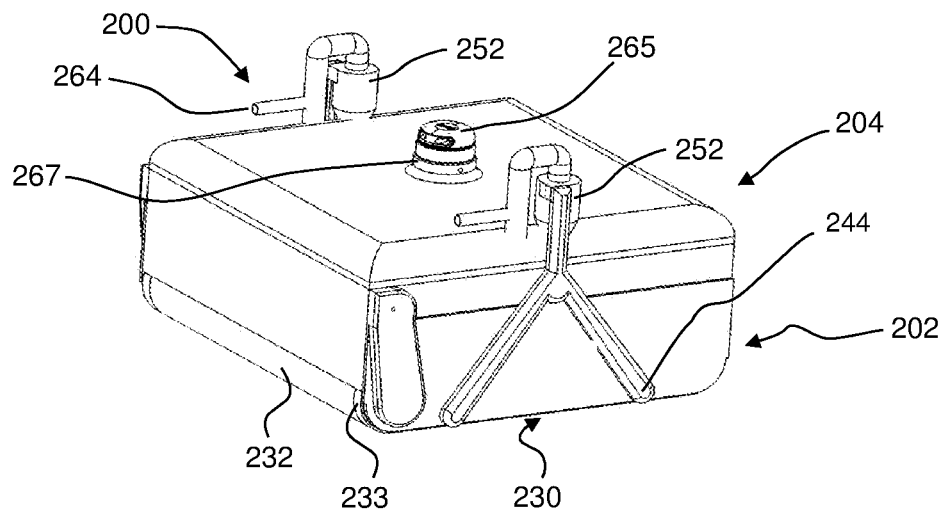
FIG. 3 illustrates an exterior embodiment of a device.
Figure 3B:
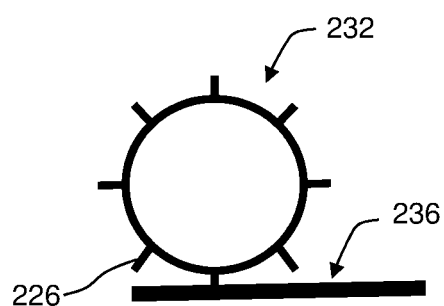

FIGS. 1 and 2 show schematically a mobile disinfection device 200 according to an embodiment of the invention. The device is divided into two main sections: (i) a lower portion 202 comprising a disinfection chamber 203 and associated hardware and (ii) an upper cabin 204 carrying auxiliary components, such as battery 214 etc. The disinfection chamber 203 is conveyed along a surface 236 to be disinfected by a propulsion system 228 (FIG. 9) while preventing radiation leakage through the wall of the disinfection chamber 203, which is formed of a material that is impervious to the radiation and acts as a peripheral shielding 207.

The disinfection chamber 203 defines a closed upper end 205, an open lower end 206 (FIGS. 4 and 5) and a surrounding wall 207 having opposing front and rear portions and opposing side portions. Respective lower front, rear and side edges of the wall 207 are supported by the propulsion system above the surface to be disinfected, typically leaving a slight air gap so as to reduce frictional contact between the disinfection chamber 203 and the surface 236. One or more radiation sources 260 are mounted inside the disinfection chamber for irradiating the surface 236 through the open lower end 206. For effective disinfection, UV radiation is commonly used and it is then necessary either to disable the radiation source in the presence of people as is commonly done in known systems; or to prevent leakage of the UV radiation so that the device can still be used even when people are located in close proximity to the device.

To this end, the wall 207 of the disinfection chamber defines a peripheral shield that is impervious to the radiation and the propulsion system 228 is configured to obstruct radiation that might otherwise escape from inside the disinfection chamber at the lower edges of the wall 207. The propulsion system 228 may comprise a pair of mutually parallel front and rear rollers 232 whose respective outer surfaces are configured to obstruct radiation that might otherwise escape from inside the disinfection chamber. The propulsion system further comprises a pair of belts 233, each overlapping the front and rear rollers at opposite ends thereof and configured to obstruct radiation that might otherwise escape from inside the disinfection chamber. The propulsion system is configured to drive the belts so as to convey the device along the surface while inhibiting radiation leakage through any gaps that may form between the surface and the lower edge of the disinfection chamber.

These features are seen more clearly in FIGS. 17A and 17B, which actually show schematically side and end elevations of the device according to a different embodiment described below with reference to FIG. 12, wherein the disinfection chamber includes a main outer chamber and an auxiliary inner chamber to provide additional sealing. However, the manner in which the propulsion system blocks radiation is the same for both embodiments. Thus, referring to FIG. 17A and ignoring for the time-being the inner chamber 300 shown in dotted outline, it is seen that the propulsion system 228 raises the lower edge of the disinfection chamber slightly above the surface 236 thereby forming an air gap 231, through which radiation could conceivably leak and expose a person nearby. However, the outer surface of the roller serves as an obstruction to such radiation thereby preventing or at least very significantly reducing radiation leakage in the direction of travel of the device. Likewise, FIG. 17B shows that the belts 233 serve as an obstruction to radiation that might otherwise leak through the air gap 231 between the surface 236 and the lower side edges of the disinfection chamber.

The size of the air gap 231 will, of course, depend on the diameter of the rollers 232 and the height from the lower edge of the disinfection chamber where their shafts are located. In preferred embodiments, the geometry is such that a small air gap persists so that when the device travels, the lower edges of the disinfection chamber are raised above the surface so as to avoid frictional contact and thus facilitate motion of the device. But the invention does not belie the possibility that the rollers are dimensioned and located to leave substantially no gap. Even in such case, bumps along the surface being disinfected can cause the device to tilt, thereby creating a gap between the surface and at least one lower edge of the disinfection chamber. However, also in this case, radiation leakage will be obstructed by the outer surface of the rollers and belts.

Figure 7:
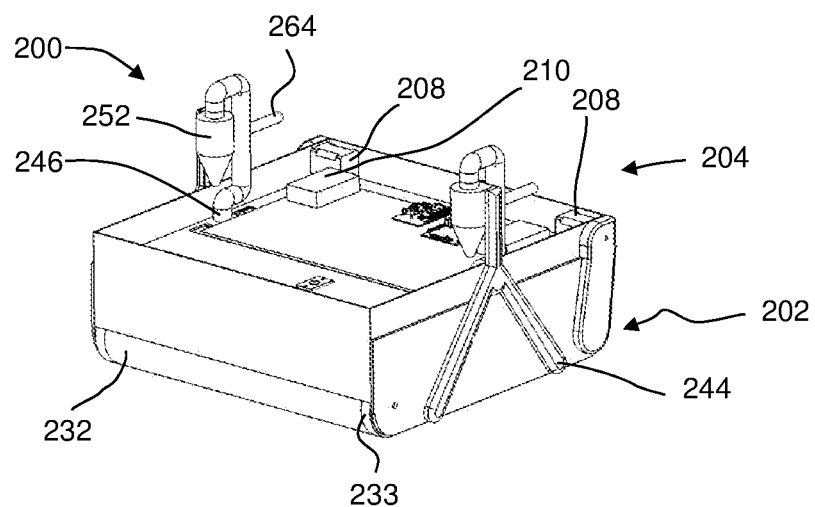
FIG. 7 illustrates an upper side of a device, without the cover.
Figure 8:
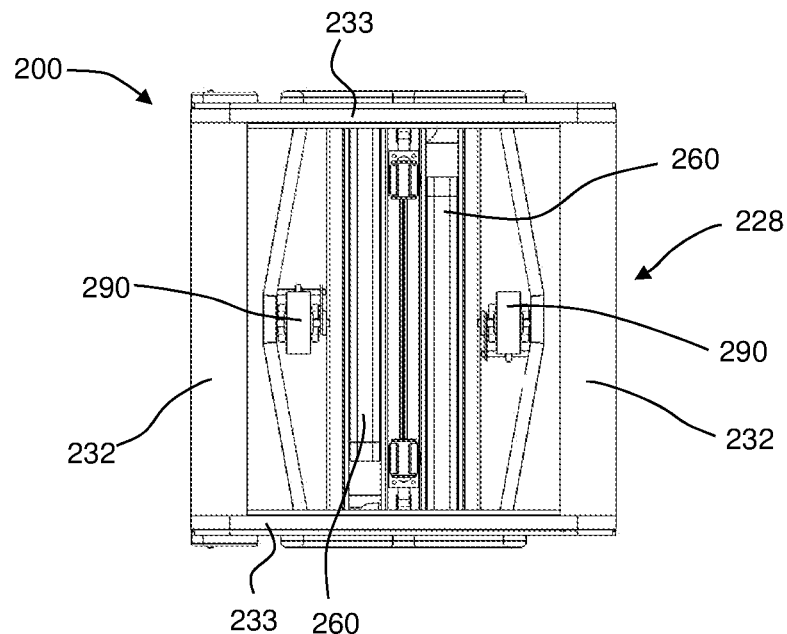
FIG. 8 illustrates a bottom view of a device.

Reverting to FIGS. 1 and 2, it is seen albeit only schematically that the peripheral shielding 207 constituted by the side wall of the disinfection chamber 203 has adjustable sealing lips 215 at its lower edge that create a dark and captured space 234 with the surface 236 carrying the device. The sealing lips 215 are adjustable by a controller 237 so as to effect minimal frictional contact with the surface 236 while effectively closing the gap between the surface and the lower edge of the sidewall of the disinfection chamber, thereby preventing leakage of UV radiation. The meaning of "dark" for this description is that no UV light is scattered out and no visible light penetrates therein. At least one closed-loop vacuum dust cleaning unit 242 is carried by the cabin 204 and has air inlet(s) 244 and air outlet(s) 246 openings (also shown in FIG. 9) interfacing with the captured space 234. The vacuum unit 242 has at least one air blower 248 driven by an electric motor 250. In FIG. 1, the controller 237 is shown schematically coupled to the UV source electronics 212, but it will be appreciated that other components such as the air blower 248 and the electric motor 250 are also controlled by the controller 237. The blower 248 circulates, in a closed loop, air sucked from the captured space 234 through the inlet opening(s) 244 via cyclonic dust separator(s) 252 (also in FIG. 7) and via a heat exchange section 217 and discharges the air back into the captured space 234 via air outlet opening(s) 246. The captured space 234 is isolated from the surrounding by the peripheral shielding (FIG. 9) to avoid scattering of the UV radiation 262 and to control the air leakage, from the captured space 234 to the surrounding of the device, of the discharged air coming from the outlet 246.

The heat exchange section 217 transfers the heat 218 generated by the device elements, such as motors 208 and 250, drivers 210, battery 214, UV source electronics 212 and possibly any other heat source onboard the device to the circulating air in order to increase the air temperature and to facilitate moisture removal from the surface 236.

It should be clear that the heat exchange section 217 in a FIG. 1 is for illustration purpose only—this section may be concentrated at a single location, as shown in a FIG. 1, or it may by split to a number of locations along the airflow path. When the heat exchanger is split, the possible heat exchange locations may be, but are not limited to: at the motor 250 body by heat exchanging fins (the motor must be positioned inline the airflow, as shown in FIG. 1); at the cyclonic separator 252 envelope which has a significant heat exchange area with the airflow inside the cyclone (for this, the cyclone body should be formed from a conductive material such as metal); at the disinfection chamber 203 which most probably will be a convenient place for many of the heat-generating components in the device, as it shown in FIGS. 3 to 9; near the UV source 260, by directing the discharged air via the UV source 260.

The need to convey the heat energy of the device 200 and its components to the circulating air, and to facilitate moisture removal from the surface 236, also requires preventing undesired thermal transfer from the device 200 and its components to the surrounding. This can be achieved by applying thermal insulation (not shown) to the device 200 and to its external components. Commercial thermal insulation solutions are well-known and therefore not described in further detail. The thermal insulation may also be configured to suppress the noise signature of the device in order to minimize disturbance to humans in the vicinity of the device (e.g. in hospitals and public facilities).

It should be noted that the UV radiation source 260 in combination with ongoing energy recirculation by utilizing the heat exchange section 217, in its concentrated or split form, and by applying the thermal isolation as stated above, may create a combined attack effect of UV and extreme temperature rise that may, together, increase the probability of killing microorganisms.

Another derivable feature of recirculating the heat energy 218 of the device 200 and applying the thermal isolation as stated above is a reduction in noise signature. This feature is especially significant in the presence of humans, as may happen in public facilities (e.g. hospitals).

In order to control the air temperature and leakage direction via the lips 215, the vacuum unit 242 is configured to direct some of the after-cyclone(s) 252 air into the bleeding air discharge 264 sub-channel (also in FIG. 3). This allows controlling the air temperature inside the captured space 234 at the desired level and retaining the air pressure inside the captured space 234 lower than the surrounding pressure. The bleeding air discharge 264 may be controlled, preferably, by an air blower 266 driven by an electric motor 268 and controlled by the controller 237, or simply by the size of the discharge pipe nozzle 270. The size of the discharge pipe nozzle 270 may be fixed or variable (not shown).

In order to ensure that the bleeding channel air is free of any kind of contaminations, the bleeding air discharge 264 outlet may be at least indirectly connected to a UV disinfection chamber 272 (in FIG. 1 only), thus ensuring bleeding air disinfection by a secondary UV source 274 prior to final discharge into the surrounding atmosphere.

In order to further clarify the safety mechanism principles, a simplified schematic of the mechanism is illustrated in FIG. 2. To monitor the scattering UV radiation 262 escaping from the captured space 234 via the sealing lips 215 to the surrounding atmosphere, at least one light sensor 280 is coupled to the interior structure of the captured space 234 to monitor the visible spectrum external light penetrating into the captured space 234 via the peripheral shielding 207 and its lips 215. This at least one light sensor 280 is connected to the controller 237 and is configured to sense light in the visible spectrum that penetrates into the captured space 234 from the surrounding. At normal operational conditions, when the sealing lips 215 of the peripheral shielding 207 contact the surface 236 tightly, the inside of the captured space 234 should be completely dark and the light sensor(s) 280 should indicate near zero visible light spectrum energy. It may be assumed that visible light penetration from outside the device 200 into the captured space 234 is generally proportional to UV radiation scattering from the captured space 234 via the peripheral shielding 207 and via its sealing lips 215 to the surrounding. To support light sensor 280 functionality in dark or near dark environments, visible spectrum light sources (e.g. LED or bulb) 282 can be attached to the exterior of the device 200 envelope to provide supplementary light energy 222 in order to reduce the dependency on external light conditions. Alternatively, infrared light may be used and therefore within the context of the invention and the appended claims wherever the term "visible" is used in association with "visible light" or "visible spectrum" it is to be understood that this includes infrared. The light sensor 280 and the supplementary visible spectrum light sources 282 are interfaced to the controller 237 of the device 200 to control the UV source 260 power and to turn off the radiation source 260, whenever predetermined safety criteria are achieved. Another safety mechanism to provide redundant safety level is at least one angle sensor (not shown), configured to determine an angle of the device relative to the surface 236 and to provide an indication for steep angular gradient which may be evidence of external physical intervention.

The device 200 of FIG. 1 may be driven over a variety of surfaces 236, having either horizontal or vertical orientations or indeed inclined to the horizontal, by an arm (artificial or propelled by human), or by a propulsion system that includes integral mobile sealing elements, such as a pair of rollers 232, both capable of sealing the gap between the sealing lips 215 and the surface 236, and, whenever the latter is not contacting the sealing lips 215, to propel the device over the, typically horizontal, surface 236. As shown in FIGS. 3 to 9 and 17A and 17B and described above, the mobile sealing elements may also be tracks 230, comprising belts 233, wheels (FIG. 13B) and shielding.

Utilizing the tracks 230 and the rollers 232 may allow replacing the simplified sealing lips 215, illustrated in FIGS. 1 and 2, by self-disinfecting elements. Self-disinfection is highly desirable to avoid transmission of microorganisms from the surface 236 to other areas of the building. During movement and operation of the device 200, the tracks 230 and rollers 232 contact surfaces (FIG. 6), and after being in contact with the surface 236, are periodically exposed to the UV source 260 radiation. This periodic irradiation disinfects the tracks 230 and rollers 232 on the move.

The structure of the tracks 230 and rollers 232 is labyrinth-like, thus serving two main functions: a) to propel the device, b) while propelling, to prevent UV radiation 262 scattering out of the captured space 234.

To allow the track propulsion functionality, including sufficient traction and steering, the main weight of the device 200 should be carried by the tracks 230. This implies that the weight of the device carried by the rollers 232 should be significantly lower than that carried by the tracks 230. To achieve this functionality, the rollers 232 should be formed from either an elastic material, capable of deforming and increasing the traction over the tracks 230, or should comprise a flexible and dense brush 226, as schematically shown in a FIG. 3B. The second alternative allows scraping the surface 236 by the brush 226 while blocking UV radiation and preventing it scattering out.

Figure 4:
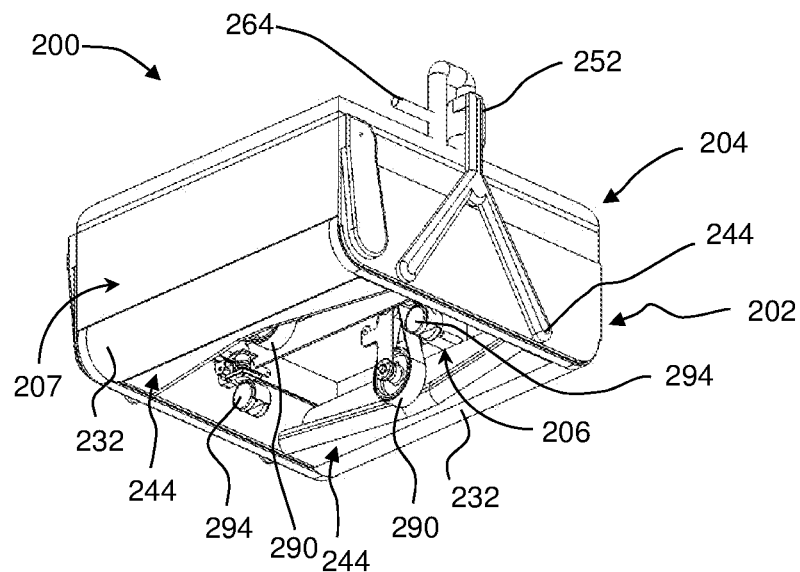
FIG. 4 illustrates a bottom part of a device.
Figure 6:
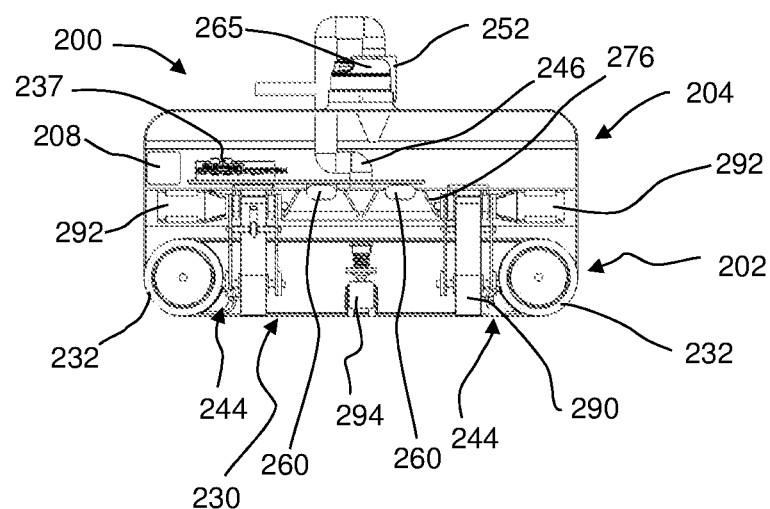
FIG. 6 illustrates a side cross-section of a device.

In order to avoid transferring microorganisms via the tracks 230 and rollers 232, as may be required in some demanding hospital scenarios, the tracks 230 and rollers 232 can be decoupled from the surface 236 by secondary propulsion wheels 290 having a lowering mechanism 292 (FIG. 6). To stabilize the device 200, two additional free wheels 294 are implemented (FIGS. 4 and 6).

The controller 237 is configured to control the cleaning and the disinfection process, in the following way: a) driving the UV source 260 at a sufficiently high power; b) driving the propulsion motors 208 at a speed allowing the device to radiate a sufficient amount of UV energy per unit of area to destroy the microorganism colonies over the surface; c) running the air blower motor 250 of the vacuum unit at a sufficient speed to achieve sufficient dirt and dust particles separation and to heat up the circulated air, utilizing the heat exchange section 217, by the heat sources, to raise the air temperature sufficiently to ensure moisture removal from the surface 236 and to facilitate destruction of the microorganisms; d) continuously monitoring by the visible spectrum light sensor 280 the visible spectrum light energy penetrating into the captured space from the surrounding, including from the supplementary light sources 282, to estimate the UV radiation 262 scattering out from the captured space and switching off the UV source 260 whenever the estimated value is beyond the safety criteria, or adjusting the power of the UV source 260 to a lower level; e) continuously monitoring the circulating air temperature and changing the bleeding air airflow by adjusting the speed of the bleeding air motor 268 or by changing the size of the discharge pipe nozzle 270.

It should be stated that the driving of the UV radiation source 260 and of the propulsion motors 208 may be done simultaneously, or at different times, based on a 'move and stop' principle, at which the UV radiation is applied only when stopped and there is no UV radiation on the move.

Figures 10A, 10B:
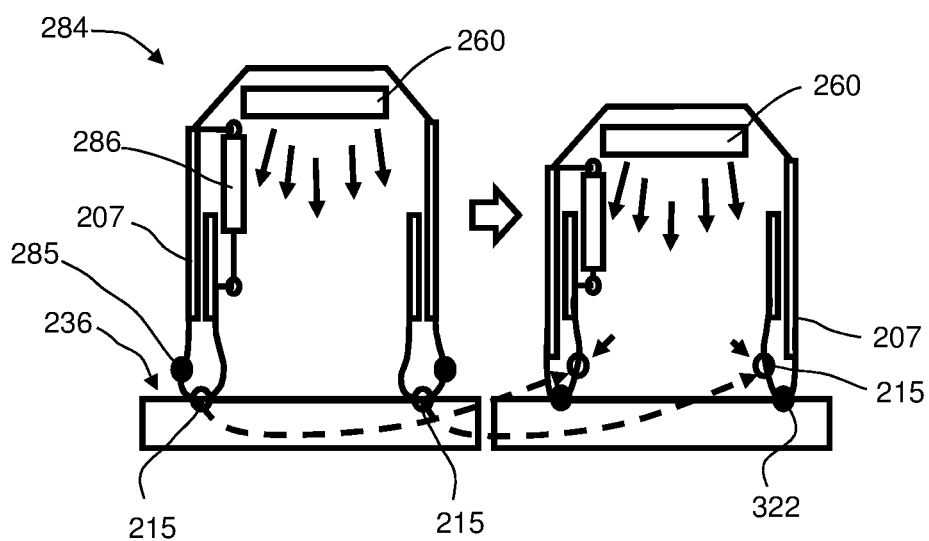
FIG. 10 illustrates a schematic reciprocal lips self-disinfection mechanism.

Whenever a 'move and stop' principle is implemented, a reciprocal self-disinfecting sealing lip mechanism 284, shown in a FIG. 10, can be implemented. The reciprocal self-disinfecting mechanism 284 allows sealing the treated surface 236 area at the 'stop' and then disinfecting the contact lines of the lips 215 by the UV source 260, while the sealing contact is created by the self-disinfecting material 285 (e.g. copper or brass) and the surface 236 (FIG. 10B). The structure of the sealing lips 215 in this embodiment is of a foldable sleeve activated by an actuator 286. The contact line of the foldable sleeve is changed by motion of the actuator 286. A closed actuator (FIG. 10B) exposes the self-disinfecting material 285 toward the surface 236. An open actuator (FIG. 10A) exposes non self-disinfecting material 215 toward the surface 236.

It should also be noted that the amount of UV radiation energy 262 deployed over the microorganisms on the surface 236 is practically unlimited, as it is a direct derivative of the UV radiation power and the propulsion speed, which can vary from zero for extremely high UV energy, to a higher propulsion speed for a moderate UV energy.

It should be also stated that the same principle applies to the thermal energy recycling: the amount of thermal energy over the microorganisms on the surface 236 is practically unlimited, as it is a direct derivative of the recycled power of the device 200 and the propulsion speed, which can vary from a zero for extremely high thermal energy, to a higher propulsion speed for moderate thermal energy.

It should be also noted that the device 200 can be autonomous or manually operated.

Whenever the device 200 is autonomous, the mapping sensors 265 (FIG. 3A) on the top of the device 200 are configured to indicate the distance to the object ahead of the device and a camera 267 (FIG. 3A) is configured to identify the object. The device 200 may also be equipped with hazard sensors (not shown) to indicate obstacles such as stairs and means responsive thereto for stopping the device.

The abovementioned sensors should not be considered as limiting the potential autonomous applications based on the present invention. Other sensor technologies may be integrated to provide a higher level of autonomous performance.

The device 200 may be equipped with a charging module and interface (not shown) for interfacing to an external recharging unit (not shown) configured to recharge the battery 214. The recharging unit is configured to provide power to the battery 214 either by wires, or wirelessly or a combination thereof. When recharging over wires, the recharging unit provides power via conductive connectors (not shown). The device 200 comprises at least one conductive receptor that is configured, when in electrical communication with at least one of the conductive connectors, to provide power to the battery 214 of the device.

It should be noted that the UV source 260 can be selected from a group consisting of: bulbs or LEDs and any combination thereof.

Figure 5:
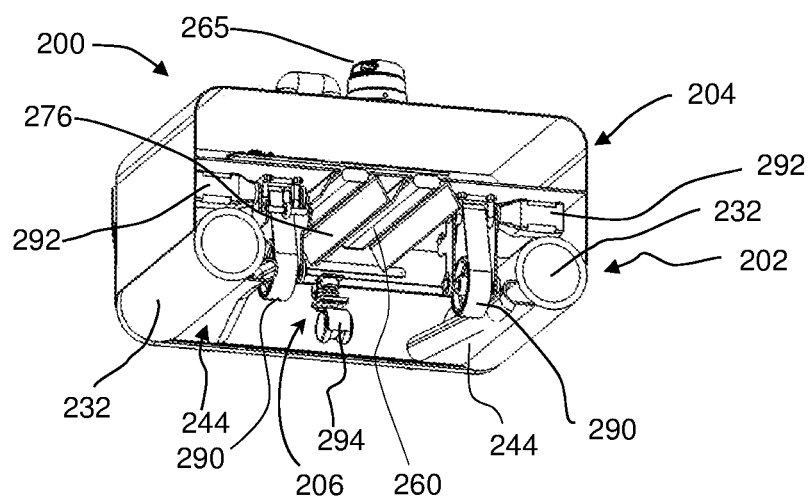
FIG. 5 illustrates a perspective cross-section of a device.
Figure 9:
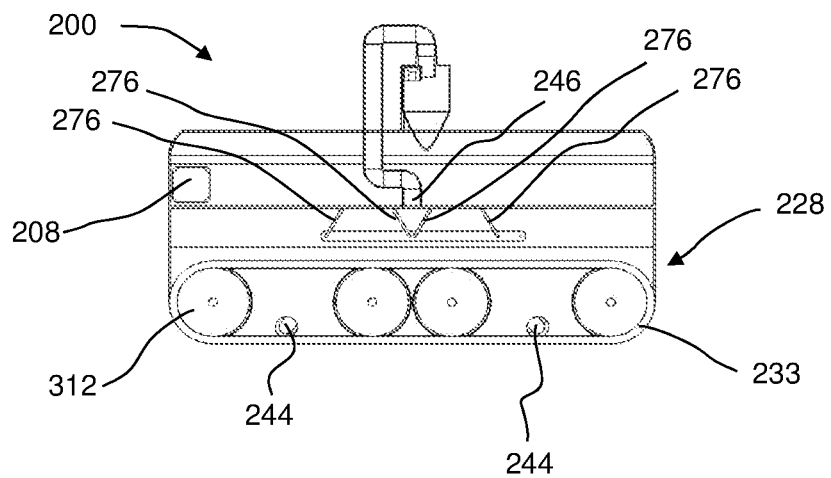
FIG. 9 illustrates a cross-section view of the device at the track area.

It should be also noted that an alternative for switching off the UV source 260 (which may shorten the bulb life) is to employ a mechanical shutter mechanism 276 shown in FIGS. 5, 6 and 9.

Figure 11:
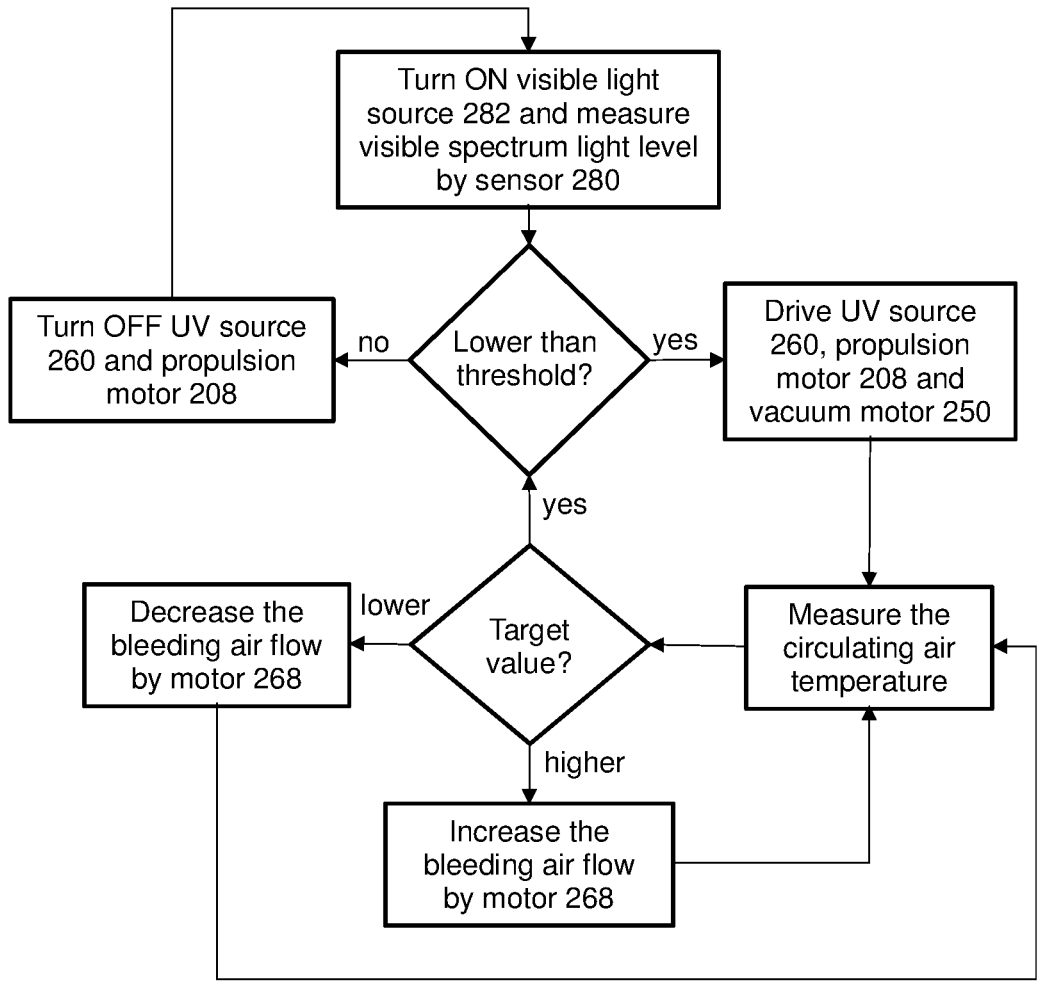
FIG. 11 illustrates the method flowchart.

The method of cleaning and disinfection proceeds in a manner very similar to that disclosed above. This method is presented by a FIG. 11 and includes: a) driving the UV source 260 at a sufficient high power; b) driving the propulsion motors 208 at the speed allowing the device to radiate a sufficient amount of UV energy per unit of area to destroy the microorganism colonies over the surface; c) running the air blower motor 250 of the vacuum unit 242 at a sufficient speed to achieve sufficient dirt and dust particles separation and to heat up the circulated air, utilizing the heat exchange section 217, by the heat sources, to a temperature sufficient to ensure moisture removal from the surface 236 and to increase the probability of killing microorganisms; d) continuously monitoring by the visible spectrum light sensor 280 the visible spectrum light energy penetrating into the captured space from the surrounding, including from the supplementary light sources 282, to predict the UV radiation scatter 262 from the captured space out and switching the UV source 260 off whenever the prediction is beyond the safety criteria, or adjusting the UV source 260 power to a lower level; e) continuously monitoring the circulating air temperature and changing the bleeding air airflow by adjusting the bleeding air motor 268 speed or by changing the size of the discharge pipe nozzle 270.

The method, as described above, may be implemented simultaneously when the device is moving and attacking the microorganisms on the move, or when the device moves, stops and attacks. The main difference between the two approaches is the rate of disinfection, which is higher when implemented simultaneously.

Figure 12:
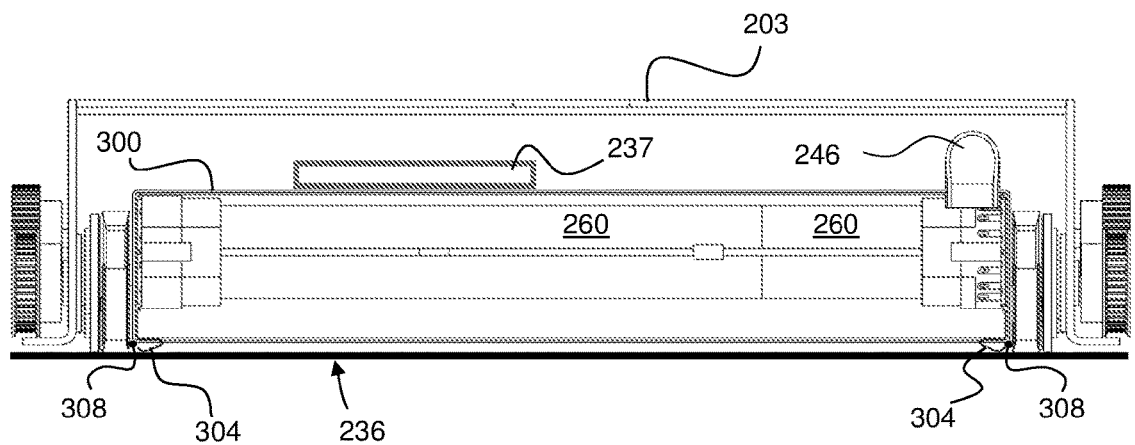
FIG. 12 is a front cross-sectional view of the system with a double UV barrier.
Figure 17A:
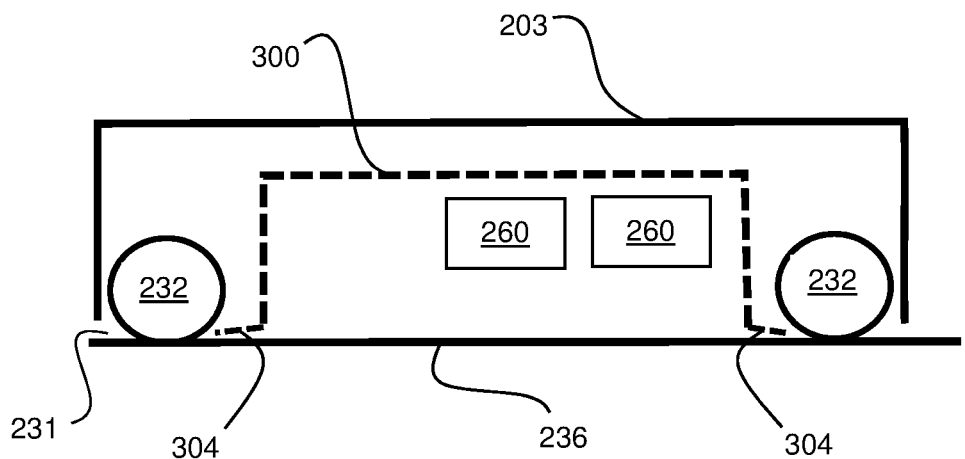
FIGS. 17A and 17B show respectively schematic side and end elevations of the device for clarifying the operating principles of the invention.
Figure 17B:
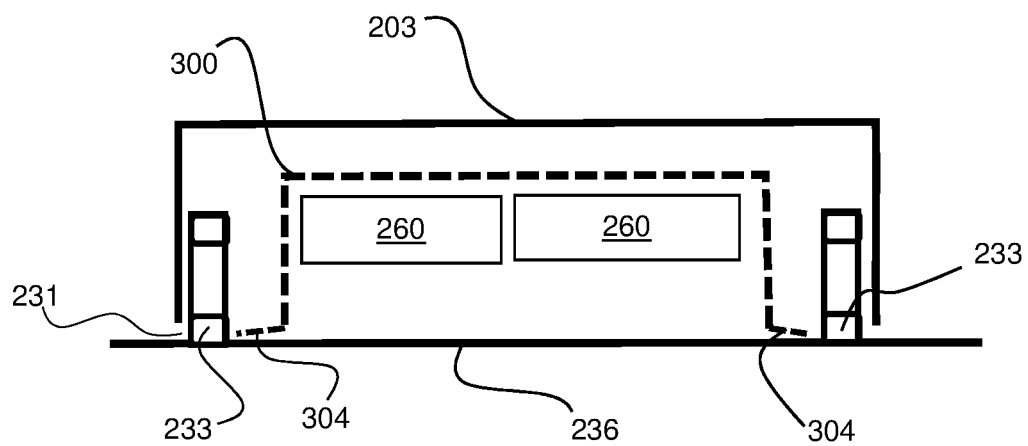

To enhance the safety level of the system, an additional, second, UV barrier shown in FIGS. 12, 17A and 17B is established by an auxiliary inner chamber 300 contained inside the disinfection chamber 203. The inner chamber 300 is in the form of an upside down box, whose open end is close to the surface 236, thus minimizing the UV radiation escaping beneath the lower edge of the inner chamber. The radiation sources are, of course, now supported within the inner chamber 300, which thus strictly speaking constitutes the disinfection chamber. However, the disinfection chamber may also be regarded as a double walled chamber having inner and outer portions. When the propulsion system 228 includes tracks having continuous belts of the kind employed by vehicles such as bulldozers, the outer chamber will most conveniently be of rectangular cross-section. But this does not dictate that the inner chamber 300 be of rectangular cross-section since it may be cylindrical or any other shape without impeding its functionality. To reduce UV radiation scattering escaping through the bottom edge, adjustable lips 304 control the gap between the chamber 300 and the surface 236. The gap can be adjusted by the air flow supplied via the air outlet of the vacuum unit 242. The higher the air flow, the higher will be the pressure gradient over both the internal and external sides of the lips 304 and the larger will be the gap. To control the gap in a closed loop, one or more UV light sensors 308 can be placed in the space between the inner chamber 300 and the outer chamber 203. The sensors 308 feed UV radiation measurements to the controller 237, which sets the vacuum cleaner air blower motor (shown as 250 FIG. 1) to a sufficient speed to increase or decrease the gap. By controlling the gap, frictional forces between the adjustable lips 304 and the surface 236 may be reduced or even eliminated. The air discharged via the outlets opening 246 is exposed to the radiation of UV sources 260, thus facilitating disinfection of the air prior to its discharge out of the inner chamber 300.

As seen for example in FIG. 17A, the radiation escaping the inner chamber 300 via the gap will enter the outer chamber 203 and be blocked by the rollers 232 and the tracks 230. To assure good contact between the tracks 230 and the surface 236, a floating track-barrier mechanism 310 is employed. Unlike in typical tracks designed to distribute platform weight over a track contact area, in the floating tracks 310 some of the platform weight is transferred to the driving wheels 312, left and right (FIG. 13B), and some to the free wheel 314, thus providing the system propulsion based on tri-wheel principle—two driving wheels 312 and one free wheel 314.

Figure 13A:
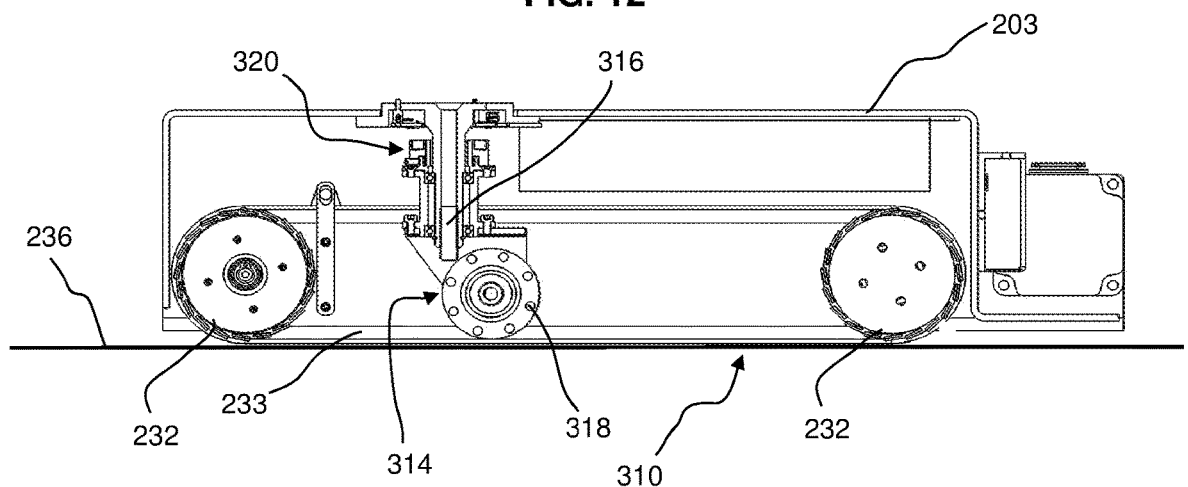

To allow measurement of the system motion vector, distance and direction, the free wheel 314 is equipped with a magnetic pick-up sensor 316 (FIG. 13A) which counts the number of exposures of the sensor 316 to metal pins 318 integrated inside the free wheel 314. The number of exposures is proportional to the distance that the free-wheel 314 moves over the surface 236. The direction of the free-wheel 314 is continuously measured by an encoder 320 integrated into the mounting assembly of the free-wheel 314 (FIG. 13A). Driving wheels 312 (FIG. 13B) are coupled to a belt pulley 322, which is driven via a belt 324 by another belt pulley attached to the shaft of a motor 208. As shown in FIG. 13C, the roller 232 may carry flexible sealing strips 330 capable of creating, simultaneously, at least two sealing lines with the surface 236, thus compensating for roughness and non-planarity of the surface 236. FIG. 13D shows a similar principle of creating more than one sealing line implemented in the belts 233 wherein two lips 332 are provided to create two sealing lines with the surface 236.

Figure 14:
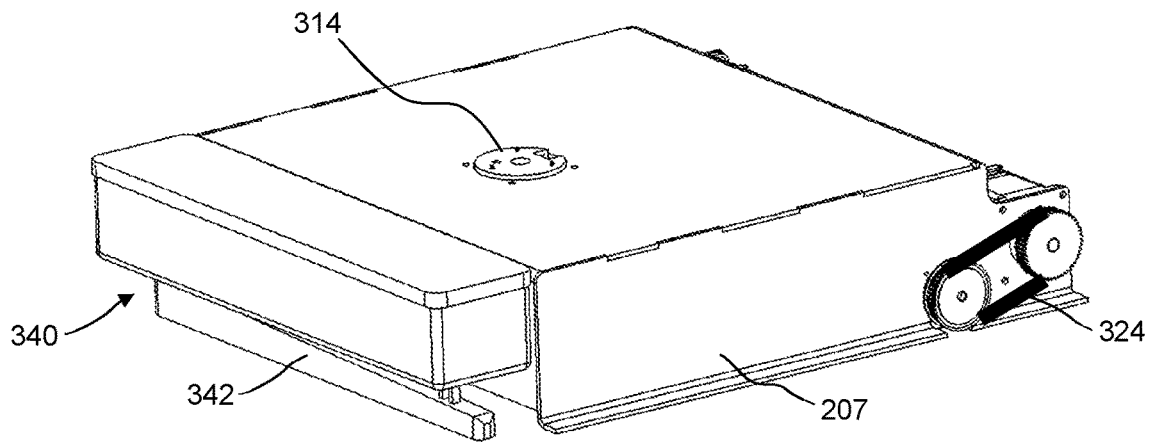
FIG. 14 is a perspective view of the system with a vacuum unit.
Figure 15A:
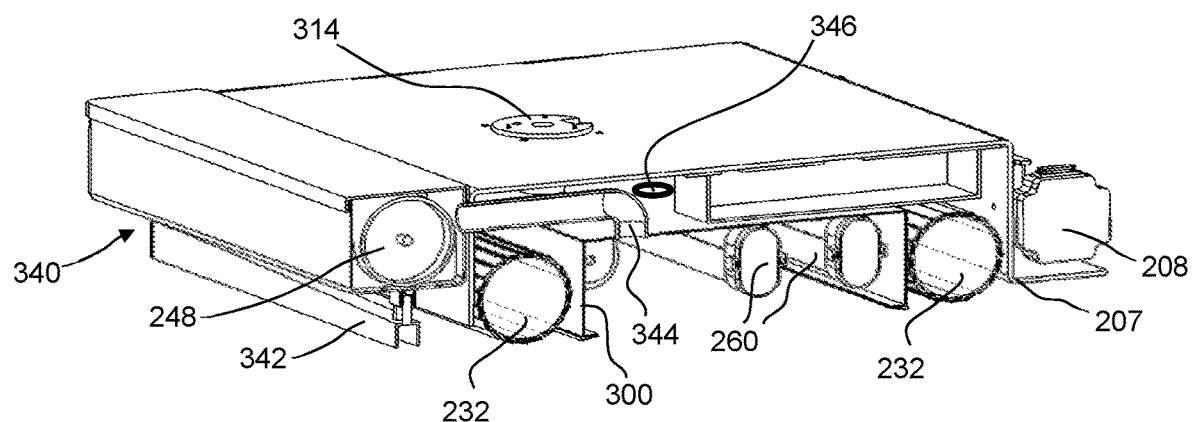
FIGS. 15A and 15B are views of the vacuum unit and its air flow lines.

To remove dust and small obstacles ahead the front roller 232, a vacuum cleaning unit 340 shown in FIG. 14 is coupled to the shielding 207. A vacuum suction duct 342 cleans the lane ahead of the roller 232 and tracks 230, to assure smooth operation and minimize the number of obstacles on the surface 236. As shown in FIG. 15A, the vacuum air-flow is in an open-loop: an air blower 248 driven by an electric motor 250 applies suction through a suction duct 342 ahead of the front roller 232 for capturing contaminated air, which is discharged into the disinfection chamber 300 by a pipe 246. To achieve faster actuation response of adjustable lips 304, a controller responsive to sensor signals can control a discharge valve 346 actuated by a servo motor (not shown). The discharge valve 346 lets the air move into the space between the shield 207 and the chamber 300 and thereby controls the amount of air flowing via the adjustable lips 304. This closed-loop control is faster and much more precise than control based on power/speed regulation of the air blower motor 250 described above.

Figure 15B:
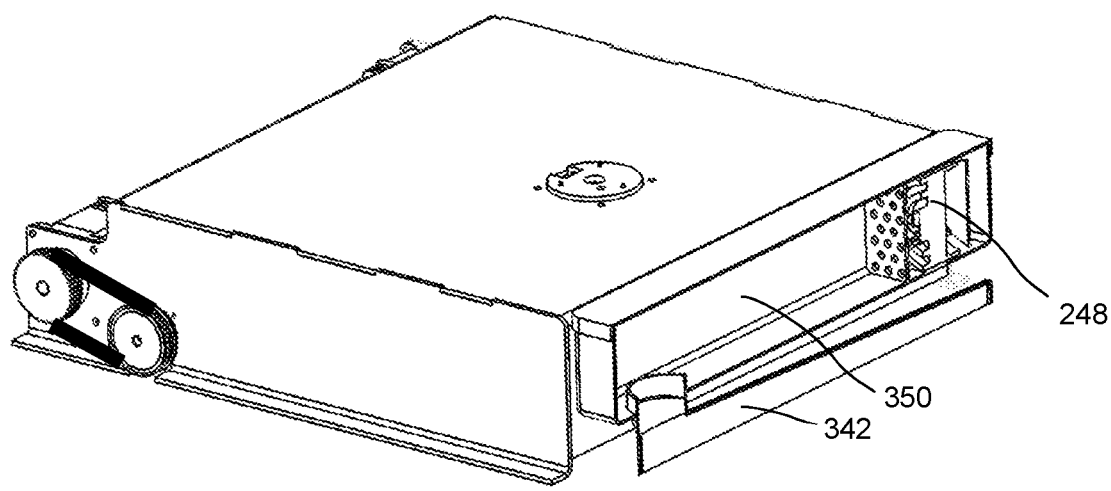

FIG. 15B shows pictorially in cross-section the main features of the vacuum unit 340. After being sucked through the duct 342, the air flows via a bag filter (not shown) located inside a filter compartment 350 and then directed by the air blower 248 into the pipe 246.

Figure 16:
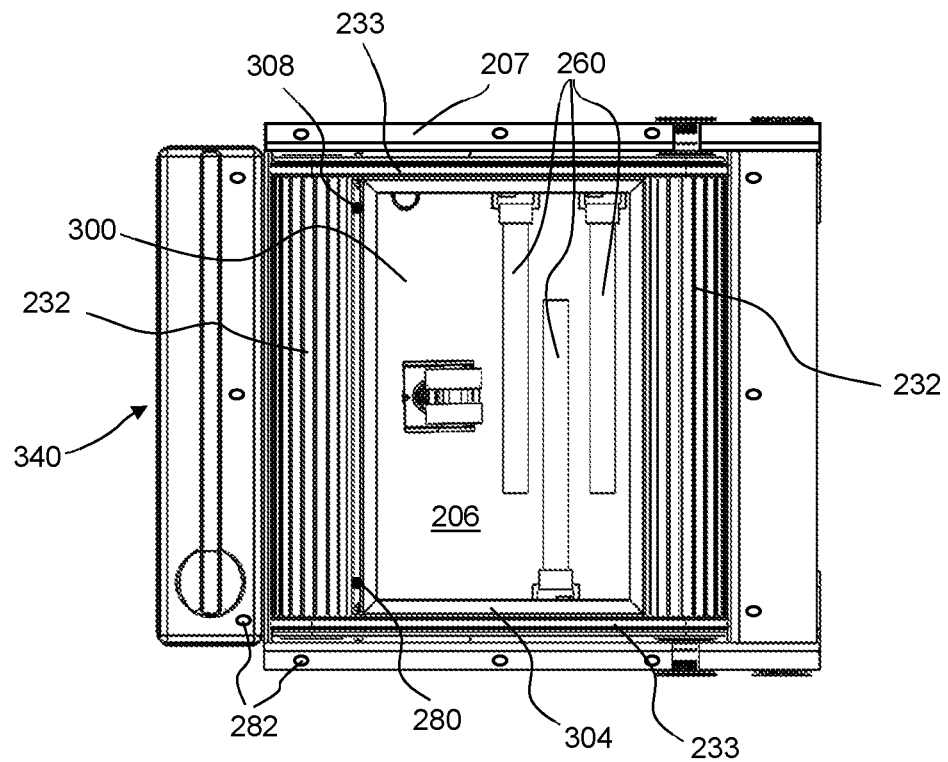
FIG. 16 is a bottom view of the system with the LED arrangement.

FIG. 16 shows an arrangement of the UV light sensors 308 and visible spectrum light sensors 280 are located in between the shielding 207 and the disinfection chamber 300, or more precisely, between the floating track-barrier mechanism 310 and the auxiliary chamber 300. Visible spectrum light sources (LED) 282 are coupled to the shielding 207 margins and to the vacuum unit 340.

The description of the above embodiments is not intended to be limiting, the scope of protection being provided only by the appended claims.

It is to be noted that the terms "upper" and "lower" as used in the foregoing description when applied to the ends of the disinfection chamber define their orientation relative to the surface being disinfected. Thus, when the device is used to disinfect a horizontal surface, such as a floor, these terms also correspond to their actual orientation in space. However, when the device is configured for riding on a surface that is not horizontal, such as a vertical wall, the "lower" open end of the disinfection chamber will now be vertical and adjacent to the wall surface, while the "upper" end will be remote from the wall surface. Therefore, in the claims, the "lower" and "upper" ends are referred to as "proximal" and "distal" respectively, which are equally applicable regardless of whether the device is horizontal or inclined to the horizontal during actual use.

Although the device has been described with particular regard to a UV radiation source, it will be appreciated that the principles of the invention are equally applicable to other potentially hazardous radiation sources.

Features described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

The invention claimed is:

1. A mobile disinfection device, comprising:
 a disinfection chamber coupled to a propulsion system configured for moving along a surface to be disinfected, said disinfection chamber defining a closed distal end, an open proximal end and a surrounding wall having opposing front and rear portions and opposing side portions,
 a radiation source mounted inside the disinfection chamber for irradiating said surface through the open proximal end;

the wall of the disinfection chamber defining a peripheral shielding impervious to the radiation;

the propulsion system comprising a peripheral seal surrounding a proximal edge of said wall and being configured to obstruct radiation that might otherwise escape from inside the disinfection chamber, at least one light sensor inside the disinfection chamber configured to monitor visible light penetrating into the disinfection chamber through the open proximal end; and a control device coupled to the at least one light sensor and responsive to visible light entering through the proximal end of the chamber for turning off the radiation source.

2. The device according to claim 1, wherein the propulsion system comprises: a pair of mutually parallel front and rear rollers, and a pair of belts, each overlapping the front and rear rollers at opposite ends thereof; and wherein respective outer surfaces of the rollers and the belts are configured to obstruct radiation that might otherwise escape from inside the disinfection chamber; the propulsion system being configured to drive the belts so as to convey the device along the surface.

3. The device according to claim 1, comprising:
at least one supplementary visible light source mounted external to the chamber and configured to supplement ambient light, whenever a level of the ambient light is less than a predetermined threshold.

4. The device according to claim 1, further comprising at least one hazard sensor configured to determine a safety hazard; the control device being responsive to the hazard sensor for blocking radiation escaping from the disinfection chamber.

5. The device according to claim 3, wherein said at least one supplementary visible light source is interfaced to said control device for radiating at a power sufficient to estimate the UV scattering.

6. The device according to claim 1, wherein the radiation source is selected from a group consisting of: UV bulbs or UV LEDs and any combination thereof.

7. The device according to claim 1, being configured to move over the surface driven by an arm at least indirectly coupled to the distal end of the disinfection chamber.

8. The device according to claim 1, wherein:
the wall of the disinfection chamber comprises an inner wall and an outer wall, and the propulsion system is configured to obstruct radiation that might otherwise escape through the outer wall of the disinfection chamber, and the peripheral seal surrounds a proximal edge of the inner wall.

9. The device according to claim 1, wherein the peripheral seal is irradiated, on the move, by the radiation source after contacting said surface to avoid transfer of microorganisms conveyed by said surface to the peripheral seal to a subsequent location.

10. The device according to claim 1, wherein the peripheral seal may be decoupled from the surface to avoid transmission of microorganisms by the peripheral seal to a subsequent location.

11. The device according to claim 1, wherein the proximal end supports adjustable sealing lips, allowing control of a gap between the sealing lips and the surface.

12. The device according to claim 11, wherein at least a portion of said adjustable sealing lips is made of self-disinfecting material, which after being in touch with said surface undergoes a self-disinfection process, wherein said sealing lips are movable by a reciprocal mechanism allowing disinfection of said sealing lips while the self-disinfecting material contacts the surface to seal the gap and avoid radiation scattering to the surrounding during the disinfection of the sealing lips.

13. The device according to claim 8, wherein:
the peripheral seal includes adjustable lips, allowing control of a gap between the lips and the surface, an air blower driven by an electric motor is provided for conveying high pressure air to the lips for controlling said gap, radiation sensors are disposed in a space between the inner chamber and the outer chamber for obtaining radiation measurements within said space, and the air blower is responsive to said radiation measurements for operating at sufficient speed to increase or decrease the gap as required.

14. The device according to claim 1, further comprising at least one vacuum unit including:
an air inlet and an air outlet both interfacing the disinfection chamber, at least one air blower driven by an electric motor for sucking air through the inlet into and circulating air inside the disinfection chamber, via at least one cyclonic dirt and dust separator and via a heat exchanging section back to the captured space, wherein said air is discharged via air outlet opening(s);

said heat exchanging section is configured to transfer the electrically generated heat from the device heat sources to the circulating captured air to increase the air temperature thus facilitating moisture removal from the surface; and the heat sources are selected from a group consisting of: air blower motors, propulsion motors, motor and UV sources drivers, battery, and any other electric element fed by the energy of the device.

15. The device according to claim 14, wherein the vacuum unit, the disinfection chamber and peripheral shielding are thermally insulated to avoid energy loss to the surrounding, thus helping to maintain a desired air temperature, wherein the thermal insulation is configured to suppress a noise signature of the device in order to minimize disturbance to humans in the vicinity of the device.

16. The device according to claim 14, being configured to utilize accumulated energy for the removal of moisture content from said surface and to attack microorganisms on said surface by an elevated temperature rise in order to kill the microorganisms.

17. The device according to claim 1, wherein the radiation source is a UV radiation source.

18. The device according to claim 11, further including a motor-driven air blower for conveying high pressure air to the sealing lips for controlling said gap.

19. The device according to claim 11, wherein the sealing lips are adjustable by a control device so as to effect minimal frictional contact with the surface while effectively closing the gap between the surface and a proximal edge of the wall of the disinfection chamber, thereby preventing leakage of radiation.

* * * * *